July 30, 1957 E. M. WAGNER Plant Pat. 1,623
PEACH TREE
Filed Sept. 4, 1956
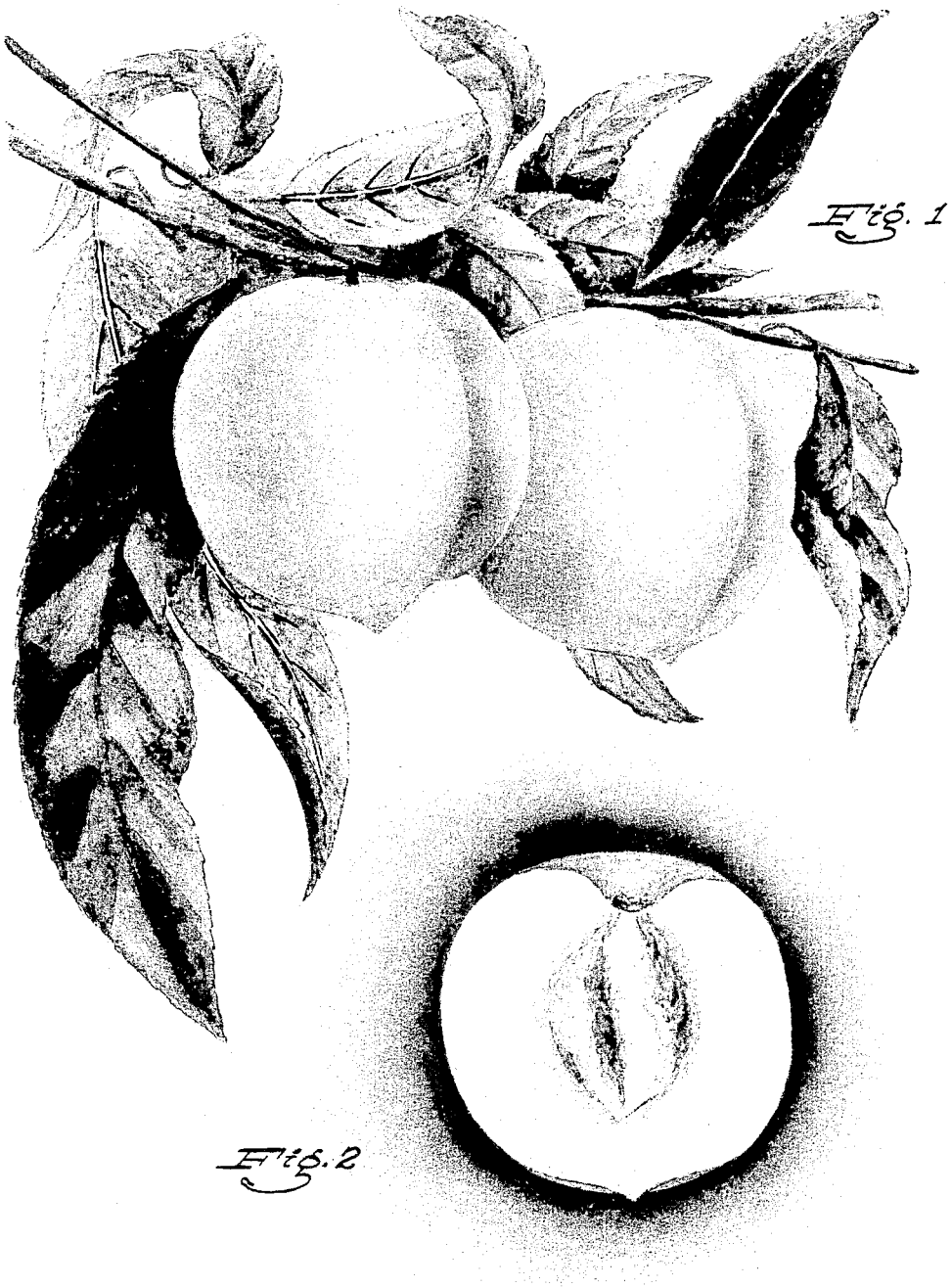
WITNESS
Addison E. Avery
INVENTOR
Edwin M. Wagner
Webster & Webster
ATTYS.

United States Patent Office

Plant Pat. 1,623
Patented July 30, 1957

1,623

PEACH TREE

Edwin M. Wagner, Sacramento, Calif.

Application September 4, 1956, Serial No. 607,967

1 Claim. (Cl. 47—62)

The present variety of peach tree is primarily characterized—as to novelty—by its fruit of yellow fleshed, clingstone type, and which is relatively late ripening, very firm fleshed, and excellent for the commercial market; all as more specifically set forth hereinafter.

Such fruit—while having general similarity to the Phillips clingstone peach (unpatented) in size, external appearance, and flesh color—is of different flavor and aroma; harvests approximately ten to fifteen days later; and is considerably firmer of flesh even when full ripe.

Another desirable feature of novelty of the present variety of peach tree resides in the fact that the firm flesh of the fruit makes possible transport from the field without damage, and clean cutting for canning, even when the fruit is full ripe. Also, the fruit is capable of withstanding the heat of canning without softening or losing color; i. e., does not become mushy or turn brown. This is of particular advantage when the fruit is used in canned fruit cocktail, and which is processed at a relatively high temperature.

A further feature of novelty is that the fruit can be held in refrigerated storage—for subsequent market or canning use—a considerably longer period of time than other clingstone varieties, and without material loss of flavor or food value. More specifically, the fruit of the present variety has—on test—been successfully canned after forty to fifty days in storage; this being a longer period than most other clingstone varieties remain in satisfactory condition. Also, after fifty-six days in storage the fruit was still in edible condition.

Additionally, the unusual firmness of the flesh of the fruit of the instant variety makes it an excellent peach for long distance shipping, fresh picked or after storage; the fruit arriving at its destination and for market use in good eating condition. Also, by reason of such firm flesh, together with the ability to withstand refrigerated storage over an extended time, the shipping period of the variety is correspondingly longer than that of other clingstone peaches.

Other advantages of the fruit of the instant variety are high sugar content in the green-ripe stage, providing edibility at any time between such stage and a full ripe condition; the fruit hangs well on the tree so that picking when full ripe for market, canning, or shipping is possible without ripe-drop loss; inclement weather does not cause deterioration of quality; the fresh fruit picking season is relatively long, being approximately two weeks; the texture of the fruit is fine and crisp, without coarse fibers, and which is exceptional in a late peach; and the fruit does not have those undesirable defects—common to some late peaches—such as raised sutures, excessive pistil point, irregular shape, and areas of fast deterioration or soft spots.

As to the characteristic of the fruit hanging well on the tree, it is observed that even after dead-ripe, there is no appreciable drop; the fruit even then being very tight and if unpicked will dry or shrivel on the branch.

The present variety of peach tree had its origination—and subsequent asexual reproduction—on my property at Sacramento, California, as follows:

Of a number of seedlings—the varietal type of which was unknown—grown on my property, as aforesaid, one showed exceptional promise, and it was therefore selected and replanted to provide favorable conditions of growth; such one seedling being the parent tree of the present variety.

The tree was maintained under careful observation, and when it came into bearing I recognized that the fruit was quite distinctive and had commercial potential, and I subsequently reproduced the variety by grafting onto suitable root stock. Such reproductions have—in all respects, including the fruit—been found to carry forward all of the characteristics of the parent tree.

In the drawings:

Fig. 1 is an elevation showing two of the fruit, together with twigs and leaves.

Fig. 2 is a sectional elevation of the fruit with the cling stone partially exposed.

Referring now more specifically to the pomological details of this new and distinct variety of peach tree, the following is an outline description thereof; all major color plate identifications being by reference to Maerz and Paul Dictionary of Color:

Tree:
- *Size.*—Large.
- *Vigor.*—Vigorous.
- *Growth.*—Upright.
- *Density.*—Dense.
- *Shape.*—Generally vase shaped.
- *Hardiness.*—Hardy; not susceptible to usual leaf diseases.
- *Production.*—Very productive—an individual tree having borne over 750 pounds of fruit.
- *Bearing.*—Regular bearer.

Trunk:
- *Size.*—Stocky.
- *Texture.*—Medium.

Branches:
- *Size.*—Stocky.
- *Texture.*—Rather smooth.
- *Color.*—Generally brown—some reddish brown.

Leaves:
- *Size.*—Large. Average length, 6″ to 9″; average width, 1⅛″ to 1¼″.
- *Form.*—Lanceolate; acutely pointed.
- *Thickness.*—Thick.
- *Texture.*—Smooth.
- *Petiole.*—Medium length; medium thickness.
- *Glands.*—Average number —four. Opposite; medium size; mostly globose; reddish green; positioned on margin near petiole.
- *Margin.*—Crenate; finely serrate.
- *Color.*—Top side—medium to dark green (22–L–6, shading to 23–L–6). Under side—lighter green (21–J–6).

Flower buds:
- *Hardiness.*—Hardy.
- *Size.*—Very small.
- *Length.*—Short.
- *Form.*—Plump; free.

Flowers:
- *Blooming period.*—About April 10th in average year. Medium blooming period as compared with other varieties.
- *Size.*—Very small.
- *Color.*—Pink.

Fruit:
- *Maturity when described.*—Hard ripe.

*Date of first picking.*—September 9–10 in average year.

*Date of last picking.*—September 20–26 in average year.

*Size.*—Large. Average diameter axially, 2½" to 3"; average transversely in suture plane, 2½" to 3".

*Form.*—Uniform; globose.

*Suture.*—Shallow; extends, unbroken, on one side only, from base to apex.

*Ventral surface.*—Rounded slightly; lips mostly equal.

*Cavity.*—Rounded. Average depth, ⅜"; average breadth, 1".

*Base.*—Rounded.

*Apex.*—Short.

*Pistil point.*—Apical.

Skin:

*Thickness.*—Medium.

*Texture.*—Tough; tenacious to flesh.

*Tendency to crack.*—None.

*Down.*—Moderate; medium length.

*Color.*—Yellow (9–K–5), over-spread in part with a very even blush, shading from orange red (10–H–9) to a deeper red (4–K–11).

Flesh:

*Amygdalin.*—Wanting.

*Juice.*—Abundant.

*Texture.*—Firm; crisp.

*Fibers.*—Fine; tender.

*Ripens.*—Even.

*Flavor.*—Mild.

*Aroma.*—Distinct.

*Eating quality.*—Good.

*Color.*—An even yellow (9–K–6) from skin to surface to pit cavity; the latter likewise being yellow.

Stone:

*Type.*—Cling; adheres to flesh over entire surface.

*Fibers.*—Short.

*Size.*—Medium to small. Average length, 1⅛" to 1¼"; average breadth, ⅞"; average thickness, ⅝" to ⅞".

*Form.*—Elliptical; cuneate toward apex.

*Base.*—Straight.

*Hilum.*—Narrow.

*Apex.*—Acuminate.

*Sides.*—Equal.

*Surface.*—Furrowed throughout, with heavy deep furrows toward pistil point and dorsal side, and with fine shallow furrows near the apex. Ridged throughout.

*Ridges.*—Rounded; interrupted.

*Pits.*—Elongated.

*Ventral edge.*—Thin; without wing.

*Dorsal edge.*—Narrow.

*Tendency to split.*—Split pits rare.

*Color.*—Medium brown (7–A–12).

Use: Market; canning.

Keeping quality: Excellent.

Shipping quality: Good.

The tree and its fruit herein described may vary in slight detail due to climatic and soil conditions under which the variety may be grown.

The following is claimed:

A new and distinct variety of peach tree, as illustrated and described, characterized by heavy and regular production of large sized, yellow fleshed, clingstone fruit similar in appearance and size to the Phillips clingstone but having a ripening period averaging ten to fifteen days later, and a picking season of approximately two weeks' duration; further characterized by fine, crisp flesh which remains very firm to and including the full-ripe stage, has high sugar content at the hard-ripe stage, and maintains its firmness and color under canning temperatures; and additionally characterized by fruit which hangs well on the tree beyond full ripe, withstands relatively long refrigerated storage without deterioration, and is of good long distance shipping quality, fresh picked or after refrigerated storage.

No references cited.